(12) United States Patent
Takehara et al.

(10) Patent No.: US 6,459,930 B1
(45) Date of Patent: Oct. 1, 2002

(54) DEHYDRATION CONDITION JUDGING APPARATUS BY MEASURING BIOELECTRIC IMPEDANCE

(75) Inventors: Katsumi Takehara; Miyuki Shimomura, both of Tokyo (JP)

(73) Assignee: Tanita Corporation, Tokyo (JP)

( * ) Notice: Subject to any disclaimer, the term of this patent is extended or adjusted under 35 U.S.C. 154(b) by 0 days.

(21) Appl. No.: 09/917,668

(22) Filed: Jul. 31, 2001

(30) Foreign Application Priority Data

Jul. 31, 2000 (JP) ...................................... 2000-230813

(51) Int. Cl.[7] .................................................. A61B 5/00
(52) U.S. Cl. ........................................................ 600/547
(58) Field of Search ................................ 600/547, 549, 600/587

(56) References Cited

U.S. PATENT DOCUMENTS

| | | | | |
|---|---|---|---|---|
| 4,793,362 A | * | 12/1988 | Tedner | 600/547 |
| 5,086,781 A | * | 2/1992 | Bookspan | 600/547 |
| 6,125,297 A | * | 9/2000 | Siconolfi | 600/547 |
| 6,339,722 B1 | * | 1/2002 | Heethaar et al. | 600/547 |

FOREIGN PATENT DOCUMENTS

| | | |
|---|---|---|
| JP | 10-71130 | 3/1998 |
| JP | 11-76188 | 3/1999 |
| JP | 11-318845 | 11/1999 |
| JP | 2000-23935 | 1/2000 |

* cited by examiner

Primary Examiner—Max Hindenburg
(74) Attorney, Agent, or Firm—McDermott, Will & Emery

(57) ABSTRACT

A dehydration condition judging apparatus is disclosed. The apparatus comprises a bioelectric impedance measuring device; a dehydration condition judging unit; an judgement result displaying unit; an inform time determining unit; and an informing device. The bioelectric impedance measuring device supplies an alternating current to a body of a subject and measures a bioelectric impedance value. The dehydration condition judging unit judges a dehydration condition of the subject based on the measured bioelectric impedance value. The judgment result displaying unit displays the judged dehydration condition. The inform time determining unit determines an inform time. The informing device informs the subject at the determined inform time that it is time to measure the total amount of body water.

9 Claims, 4 Drawing Sheets

DEHYDRATION CONDITION JUDGING APPARATUS BY MEASURING BIOELECTRIC IMPEDANCE

BACKGROUND OF THE INVENTION

1. Field of the Invention

The present invention relates to a dehydration condition judging apparatus for judging if a dehydration condition is occurring by measuring bioelectric impedance of a living body.

2. Prior Art

Dehydration is a condition, in which water in a living body is abnormally reduced, and it often occurs in daily life when a person is exercising or when the temperature is high because a lot of water is excreted from the body by sweating and an elevated body temperature. Especially, it is said that elderly persons are apt to experience dehydration symptoms. This is because, when one becomes older, size of muscles which contain water decreases, the amount of urine increases because the function of the kidneys deteriorates, and awareness of thirsty decreases because the senses are dulled. Another reason is that the amount of water which cells require decreases.

If dehydration symptoms are left untreated, the dehydration symptoms will gradually become worse until a serious dehydration condition is occurring. Usually, it is said that, when one third of the water in a living body is lost, the body temperature regulation is disturbed. This causes the body temperature to increase, and then water in the living body is further reduced. In other words, vicious circle is created, until at last, a heat illness occurs. A heat illness includes conditions such as heat cramp, desert syndrome and heatstroke. Sometimes all the organs in the body are affected by the heat illness.

Thus it is desired that dehydration symptoms be dealt with at an early stage to avoid the risk of a heat illness. However, people are often not aware of dehydration symptoms at the early stage, and thus it is difficult for them to judge their dehydration condition in an early stage only based on self awareness. As a result, the dehydration symptoms are left untreated, which symptoms thus gradually becomes worse, until a subject finally feels dizzy or thirsty and thus realizes he/she is not in good condition. It often happens that he/she is actually in a serious dehydration condition at the time he/she feels dizzy.

Japanese Patent Laid-Open Publication No. Hei 11-318845 discloses an apparatus for measuring the total amount of water in a body, thus allowing dehydration symptoms which a person is not aware of to be detected. This apparatus determines the total amount of body water in a living body of a subject easily by measuring a bioelectrical impedance value.

However, in a case where this apparatus is used, dehydration symptoms can not be detected if a subject measures the total amount of body water spontaneously. The subject often forgets to measure the total amount of body water, and thus dehydration symptoms can not be detected at an early stage. Especially, as stated above, when a person is exercising or when the temperature is high, or in the case of an elderly person, dehydration symptoms are apt to occur. Thus, a person should pay special attention to the possibility of the development of dehydration symptoms. However, when a person is absorbed in exercising, he/she can not concentrate at such times because of the heat and humidity, and thus forgets to measure the total amount of body water.

As regard to elderly people, they forget to measure the total amount of body water because they are not aware they are thirsty due to the dulling of their senses. As a result, it is difficult to detect dehydration symptoms at an early stage.

As above mentioned, a bioelectrical impedance value changes when the the total amount of body water changes. It is also known that a bioelectrical impedance value changes when the body temperature changes. That is, the bioelectrical impedance value decreases when the body temperature goes up, and the bioelectrical impedance value increases when the body temperature goes down. However, said conventional apparatus, calculating the total amount of body water based on the bioelectrical impedance value, does not take into consideration this fact that the bioelectrical impedance value changes when the body temperature changes. Thus, said apparatus can not determine the total amount of body water precisely, resulting in it being unable to judge the dehydration condition precisely. For example, in a case where the total amount of body water is decreased and the body temperature is raised, and thus a dehydration condition should be detected, the bioelectrical impedance value increases when the total amount of body water is decreased, while on the other hand, the bioelectrical impedance value decreases because body temperature is raised. Thus, when the bioelectrical impedance value is measured, and then the total amount of body water is calculated based on the bioelectrical impedance value to be able to determine whether a dehydration condition has occurred or not based on this calculated total amount of body water, the dehydration condition may not be detected.

Considering the above, an object of the present invention is to provide a dehydration condition judging apparatus which is capable of judging whether, with regard to a subject, a dehydration condition is occurring at appropriate times and without fail, and detecting a dehydration condition at an early stage accurately.

SUMMARY OF THE INVENTION

In one aspect of the invention, an apparatus for judging whether a dehydration condition is occurring (hereinafter a dehydration condition judging apparatus) comprises: a bioelectric impedance measuring device; a dehydration condition judging unit; an judgment result displaying unit; an inform time determining unit; and an informing device. Said bioelectric impedance measuring device supplies an alternating current to a body of a subject and measures a bioelectric impedance value; said dehydration condition judging unit judges a dehydration condition of the subject based on the measured bioelectric impedance value; said judgement result displaying unit displays the judged dehydration condition; said inform time determining unit determines an inform time; and said informing device informs the subject at the determined inform time that it is time to measure the total amount of body water.

In one embodiment of the invention, said bioelectric impedance measuring device supplies an alternating current of a single frequency. Alternatively, said bioelectric impedance measuring device supplies a plurality of alternating currents of different frequencies to the subject.

In another embodiment of the invention, the dehydration condition judging apparatus comprises a body temperature measuring device. Said body temperature measuring device measures a body temperature of the subject, and said dehydration condition judging unit takes into consideration the measured body temperature and then judges a dehydration condition of the subject based on the measured bioelectric impedance value.

In a further embodiment of the invention, the dehydration condition judging apparatus comprises an age inputting unit. Said age inputting unit has an age of a subject inputted into, said inform time determining unit then determining the inform time based on the inputted age.

In another embodiment of the invention, the dehydration condition judging apparatus comprises an action level input unit. Said action level input unit has an action level of the subject inputted into, said inform time determining unit then determining an inform time based on the inputted action level.

In another embodiment of the invention, the dehydration condition judging apparatus comprises a temperature measuring device. Said temperature measuring device measures a temperature, and said inform time determining unit then determines an inform time based on the measured temperature.

Said inform time determining unit determines the inform time based on any combination of the age of the subject, the action level and the temperature.

In another embodiment of the invention, said temperature measuring device measures the temperature again at least once in a period between the time the inform time is determined and the determined inform time, said inform time determining unit then determining another inform time again based on the temperature measured again.

In another embodiment of the invention, the dehydration condition judging apparatus comprises a humidity measuring device. Said inform time determining unit determines an inform time based on the measured temperature and humidity.

Other objects and advantages of the present invention will be understood from the following description of some preferred embodiments, which are shown in accompanying drawings:

DESCRIPTION OF PREFERRED EMBODIMENTS

Figure 1:
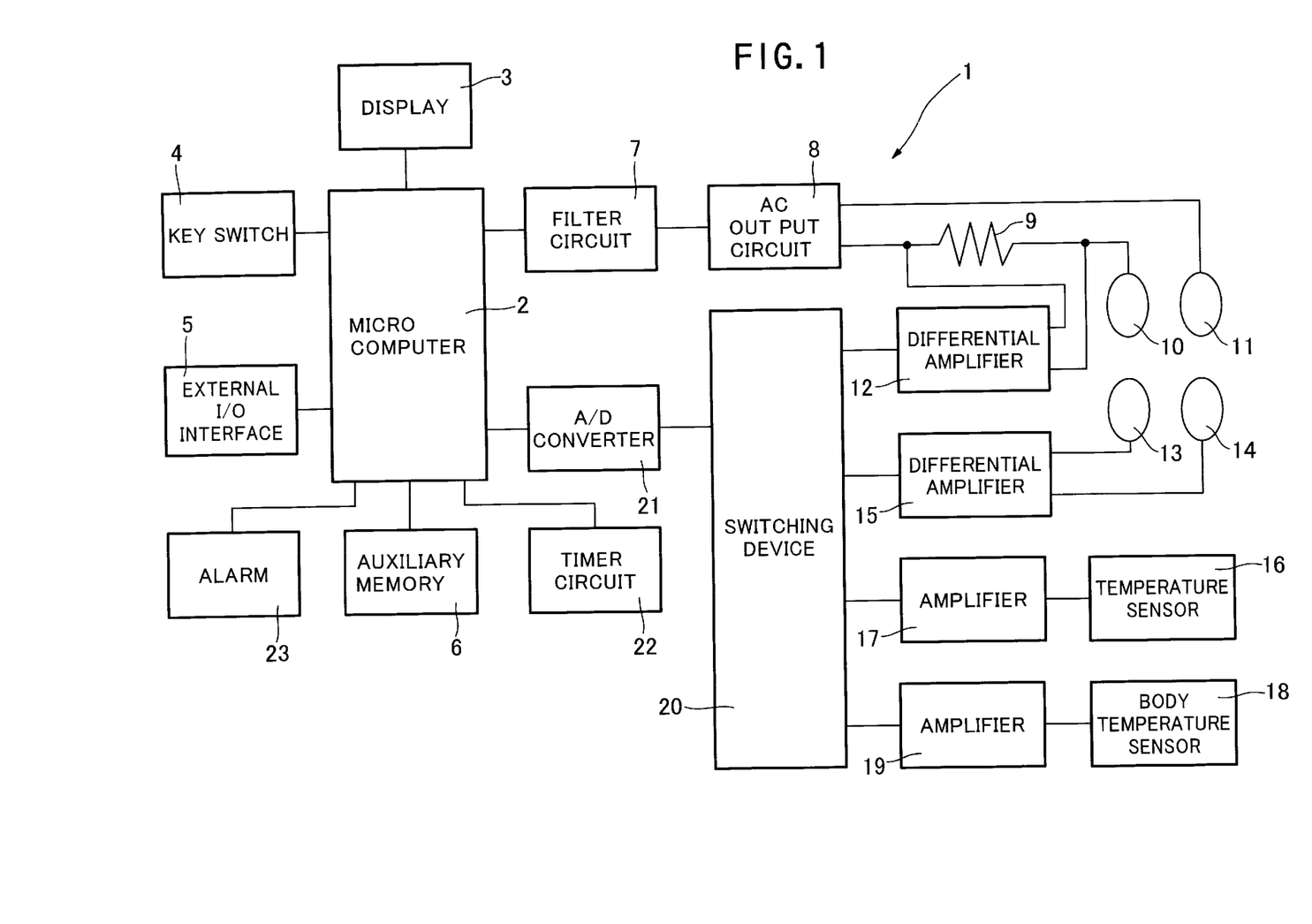
FIG. 1 is a block diagram of a dehydration condition judging apparatus according to one embodiment of the present invention.

FIG. 1 illustrates major components of a dehydration condition judging apparatus according to an embodiment of the present invention. As shown in FIG. 1, the dehydration condition judging apparatus 1 comprises a microcomputer 2 having a CPU, ROM, RAM, timer and I/O port. The CPU controls measurements and judgements, and processes the measurement data. The ROM stores programs and some parameters for control and calculation operations. The RAM temporarily stores the results of operations, the programs derived from external devices, selected parameters and the like.

The dehydration condition judging apparatus 1 further comprises a display 3, a key switch 4 comprised of key switches 4A to 4E (see FIG. 2), an external input-output interface 5, a nonvolatile auxiliary memory 6. The display 3 shows data inputted by the key switch 4, progress made in the measurements and judgement results. The key switch 4 inputs instructions for controlling the present apparatus and personal particulars required to make measurements, and selects personal particulars stored in the auxiliary memory 6. The external input-output interface 5 permits the judgement results to be transferred to external devices, and inversely it permits instructions for controlling the device and some parameters and the like to be supplied from external devices. The personal particulars and parameters relating to the measurement inputted by the key switch 4 are stored in the auxiliary memory 6. The data stored in the memory can be read out and updated.

The apparatus 1 further comprises a filter circuit 7, an AC current output circuit 8, a reference resister 9, a measuring current supply electrode 10 and a measuring current supply electrode 11. The filter circuit 7 changes waveforms to signals to be applied to a living body. The AC current output circuit 8 modifies the signals outputted from the filter circuit 7 to a predetermined effective value. The measuring current supply electrode 10 is connected to one output terminal of the AC current output circuit 8 via the reference resister 9. The measuring current supply electrode 11 is connected to the other output terminal of the AC current output circuit 8. Thus, AC current is applied through the measuring current supply electrodes 10 and 11.

The apparatus 1 further comprises a differential amplifier 12, voltage measuring electrodes 13 and 14, and a differential amplifier 15. The differential amplifier 12 detects a voltage difference between one terminal and the other terminal of the reference resister 9 in order to detect a current flowing into the body of the subject. The voltage measuring electrodes 13 and 14 detect voltage at two points on the subject. The differential amplifier 15 is connected to the voltage measuring electrodes 13 and 14 to detect a voltage difference between these electrodes.

The apparatus 1 further comprises a temperature sensor 16, an amplifier 17, a body temperature sensor 18 and an amplifier 19. The temperature sensor 16 detects an outside temperature. The amplifier 17 amplifies an output of the temperature sensor 16. The body temperature sensor 18 has a thermistor and the like to measure a body temperature of the subject. The amplifier 19 amplifies an output of the body temperature sensor 18.

The apparatus 1 further comprises a switching device 20, an A/D converter 21, a timer circuit 22 and an alarm 23. The switching device 20 outputs a selected one of the outputs of the amplifiers 12,15,17 and 19 based on the control of the microcomputer 2. The A/D converter 21 converts analogue signals outputted from the A/D converter 21 to digital signals and then outputs them to the microcomputer 2. The timer circuit 22 controls time for informing to the subject. The alarm 23 generates a sound at the inform time.

Figure 2:
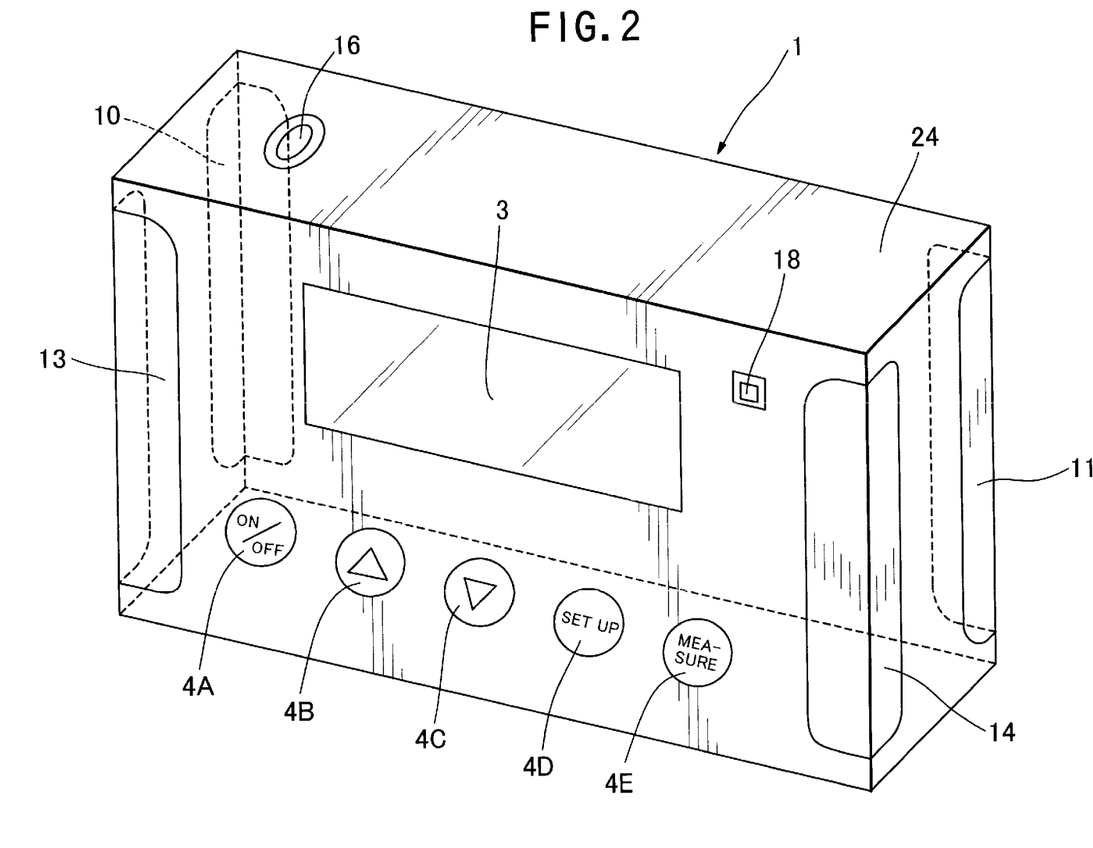
FIG. 2 is a perspective view of a dehydration condition judging apparatus shown in FIG. 1.

FIG. 2 is a perspective view of the dehydration condition judging apparatus shown in FIG. 1. As shown in FIG. 2, the apparatus 1 comprises a housing 24 which has a substantially box shape. The voltage measuring electrodes 13 and 14 and the measuring current supply electrodes 10 and 11 are disposed to be spaced apart from each other on the circumference of the housing 24. That is, the measuring current supply electrodes 10 and 11 are disposed on a left back unit and right back unit of the housing 24, respectively. The voltage measuring electrodes 13 and 14 are disposed on a left front unit and right front unit of the housing 24, respectively. The temperature sensor 16 is disposed on an upper surface of the housing 24, and the display 3, the body temperature sensor 18 and the key switch 4 are disposed on the front side of the housing 24. The key switch 4 is comprised of a power switch 4A, an up key 4B, a down key 4C, a set up switch 4D and a measurement key 4E. The power supply is turned on and off by pressing the power switch 4A. The up key 4B and the down key 4C are for selecting numerical values for inputting personal particulars. The set up switch 4D is for switching the apparatus 1 to a set up mode and inputting values which are selected by the up key 4B and the down key 4C. The measurement key 4E is for commanding the start of measuring.

Figure 3:
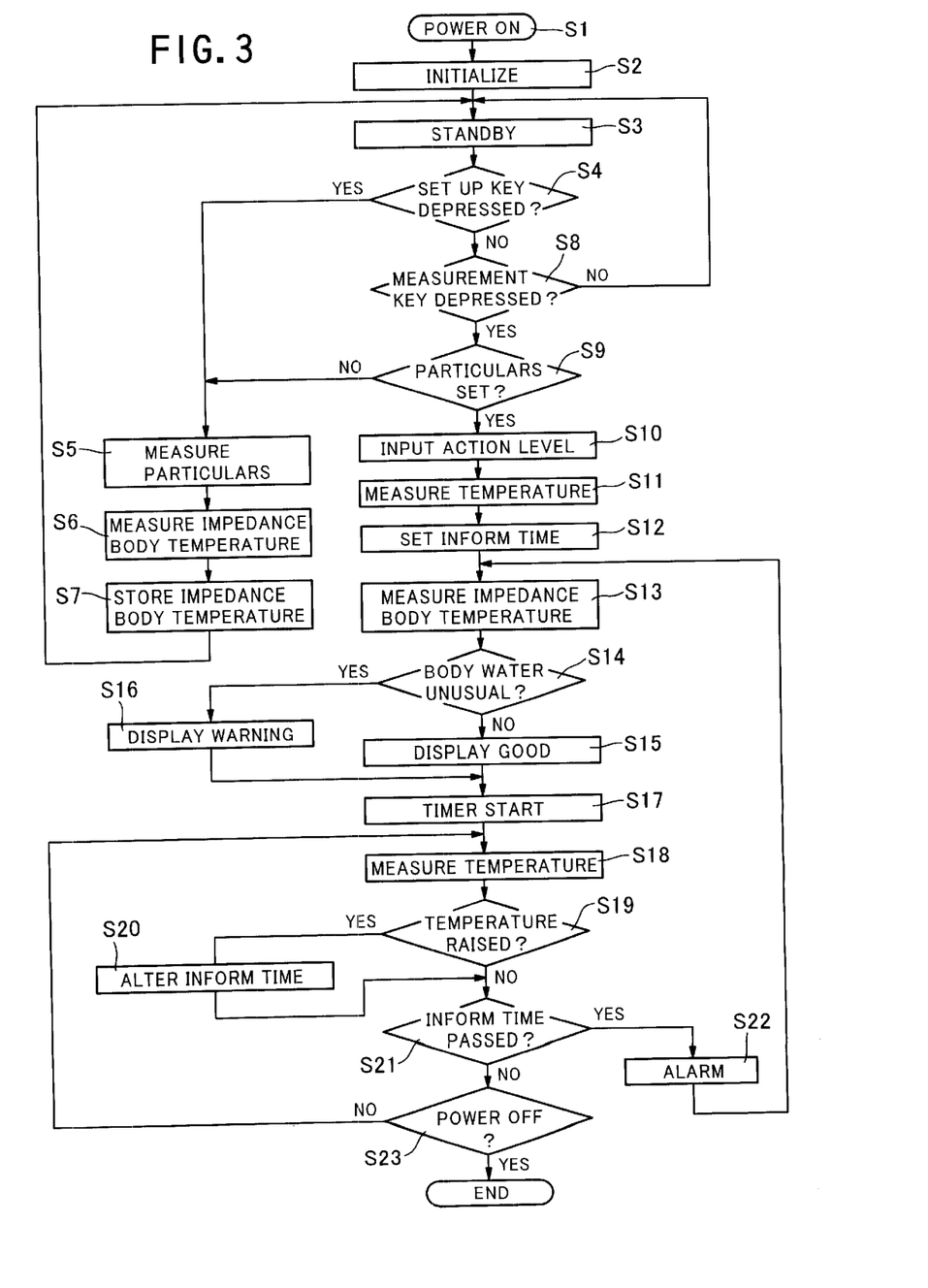
FIG. 3 is a flowchart illustrating an action flow of the dehydration condition judging apparatus of FIG. 1.
Figure 4:
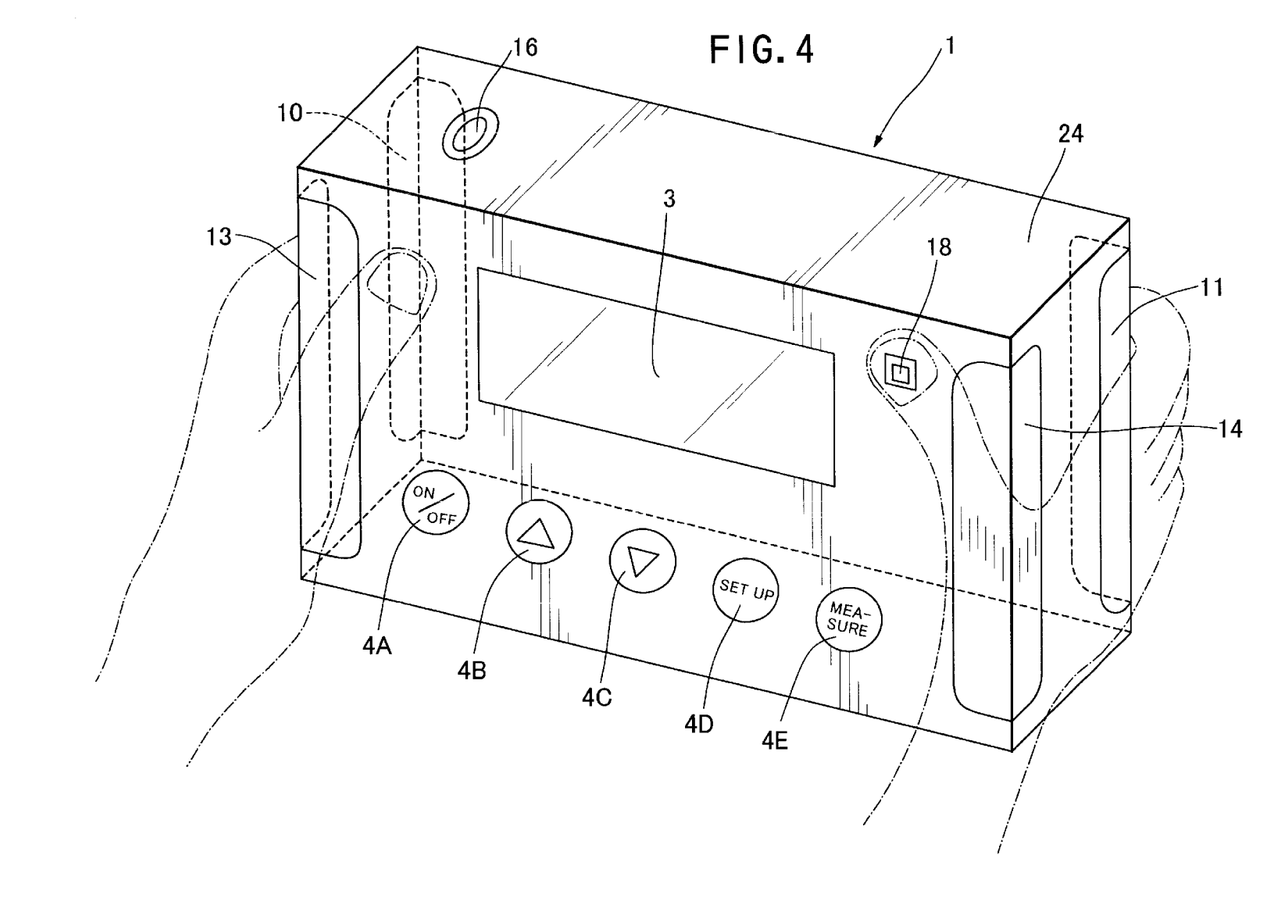
FIG. 4 illustrates the proper arrangement of a subject's hands when the dehydration condition judging apparatus of FIG. 1 is being used.

Now the operation of the dehydration condition judging apparatus will be described. FIG. 3 shows a flowchart illustrating a series of actions taken for measuring the dehydration condition. FIG. 4 illustrates the arrangement of a subject's hands when using the dehydration condition judging apparatus of FIG. 1.

When the subject depresses the power switch 4A, the apparatus 1 starts to operate (step 1) and then the apparatus 1 is initialized (step 2). Then, the apparatus 1 is changed to a standby condition, and waits for the set up switch 4D or the measurement key 4E to be depressed (step 3). If the set up switch 4D is depressed, the apparatus 1 is changed to the set up mode (step 4). Then, the subject inputs personal particulars including height, body weight, age and sex by depressing the up key 4B, the down key 4C and the set up switch 4D, and then the apparatus 1 stores these inputted personal particulars in the auxiliary memory 6 (step 5).

Then, the apparatus 1 is changed to a measuring mode. As shown in FIG. 4, the subject contacts his/her finger root of the right thumb to the body temperature sensor 18, contacts his/her other fingers to the measuring current supply electrodes 10 and 11, and contacts his/her thenars to the voltage measuring electrodes 13 and 14. The subject holds the apparatus 1 in such a way, and then depresses the measurement key 4E. When the measurement key 4E is depressed, the apparatus 1 starts to measure a bioelectric impedance of the subject.

Alternating current signals are directed from the microcomputer 2 to the filter circuit 7 based on measurement parameters. These parameters are pre-stored in the ROM in the microcomputer 2. The filter circuit 7 adjusts the waveform of the AC current to be applied to a living body. The output of the filter circuit 7 is directed to the AC current output circuit 8. The AC current output circuit 8 modifies the alternating current to a predetermined effective value. One output terminal of the AC current output circuit 8 is connected to the measuring current supply electrode 10 via the reference resister 9. The other output terminal of the AC current output circuit 8 is connected to the measuring current supply electrode 11. Thus, AC current is applied through the measuring current supply electrodes 10 and 11 to the subject.

The potentials of the both terminals of the reference resister 9 are detected by the differential amplifier 12. The differential amplifier 12 outputs potential difference values between one terminal and the other terminal of the reference resister 9 in order to detect a current flowing into the body of the subject. On the other hand, the voltages from two points on the subject are detected by the voltage measuring electrodes 13 and 14, and then supplied to the differential amplifier 15. The differential amplifier 15 outputs potential difference values between the two points of the subject. The potential difference values from the differential amplifiers 12 and 15 are switched by the switching device 20 based on the control signals supplied by the microcomputer 2, and then these values are fed to the A/D converter 21. The A/D converter 21 converts the supplied analogue values into digital values. The output of the A/D converter 21 is then supplied to the microcomputer 2. The microcomputer 2 determines the bioelectric impedance value based on these digital values.

After the bioelectric impedance value is measured, the apparatus 1 determines the total amount of body water of the subject by known method based on the measured bioelectric impedance value and the personal particulars stored in the auxiliary memory 6. At the time the bioelectric impedance value is measured, the apparatus 1 measures the body temperature of the subject by the body temperature sensor 18. That is, the value detected by and supplied from the body temperature sensor 18 is amplified by the amplifier 19, and the output of the amplifier 19 is then switched by the switching device 20 based on the control signals from the microcomputer 2, and supplied to the A/D converter 21. The A/D converter 21 converts the supplied analogue value to a digital value. The output of the A/D converter 21 is supplied to the microcomputer 2. The microcomputer 2 determines the body temperature of the subject based on the supplied digital value.

The total amount of body water determined by the above steps is used as a reference value when judging whether a dehydration condition occurs in a later step. Thus, the measurement in this step is preferably done when body condition of the subject is normal, e.g., the subject does not have a fever, and at the time when the subject is engaged in normal activities, i.e., not immediately after exercise or getting up (step 6).

The determined total amount of body water and the body temperature are stored as reference values in the auxiliary memory 6. Hereinafter, this total amount of body water is referred to as reference total amount of body water, and this body temperature is referred to as reference body temperature (step 7). After that, the apparatus 1 is again changed to the standby condition (step 3).

If the set up key 4D is not depressed in step 4, and the measurement key 4E is not depressed in step 8, the apparatus 1 continues in the standby condition (step 3). If the measurement key 4E is depressed in step 8, the apparatus 1 determines whether the reference total amount of body water, the reference body temperature and the personal particulars are stored in the auxiliary memory 6 (step 9). If these values are not stored, the apparatus 1 is changed to the set up mode (step 5).

On the other hand, if these values are stored, the apparatus 1 shows the personal particulars on the display 3 for a predetermined time, and after that shows a list of action levels instead of the personal particulars on the display 3. The action levels represent living conditions of a subject such as an exercising condition where a high level of energy is required, a normal condition where a normal level of energy is required and a sleeping condition where a low level of energy is required. The subject, by depressing the up key 4B, the down key 4C and the set up key 4D, selects and inputs an action level he/she will be at during the time he/she is controlling the dehydration condition using the apparatus 1. If the subject selects an action level which represent the exercising condition, the apparatus 1 then shows a list of different kinds of sports such as walking, running, cycling and golf on the display 3. The subject, by depressing the up key 4B, the down key 4C and the set up key 4D, selects and inputs the kind of sports he/she does during the time he/she is controlling the dehydration condition using the apparatus 1. The inputted action level is then stored in the auxiliary memory 6 (step 10).

Then, the apparatus 1 measures the outside temperature by the temperature sensor 16. That is, analogue values obtained from the temperature sensor 16 are amplified in the amplifier 17, the output of the amplifier 17 is switched by the switching device 20 based on the control signals from the microcomputer 2, and this output is supplied to the A/D converter 21. The A/D converter 21 converts the inputted analogue values to digital values, the output of which converter is supplied to the microcomputer 2. The microcomputer 2 determines the outside temperature based on the supplied digital values. The temperature thus determined is stored in the RAM in the microcomputer 2. Hereinafter, this temperature is referred to as the reference temperature (step 11).

Next, the apparatus 1 determines the inform time. The inform time is the time when the apparatus 1 should notify the subject that it is time for him/ her to examine his/her condition to judge if he/she is dehydrated. The inform time may be at the same time that the examination should take place, or it may be a little earlier than the time the examination should take place so that he/she can has time to prepare for the examination. The inform time should be determined based on the time the next examination should take place. The time the next examination should take place is preferably determined after considering factors which cause dehydration, such as age, action level and temperature.

Thus, in the present embodiment, the inform time is determined based on the age inputted at step 5, the action level inputted at step 10, and the temperature determined at step 11. If the subject is elderly, exercise in the action level is hard, or the temperature is high, dehydration condition is apt to occur, and thus the inform time is set to a short time. The inform time thus determined is stored in RAM (step 12).

After the inform time is set, the apparatus 1 is changed to the measurement mode, and, as explained in the above section on step 6, when measurement key 4E is depressed, the apparatus 1 measures the bioelectric impedance value and a body temperature. Then, the apparatus 1 corrects the bioelectric impedance value based on the measured body temperature using the reference body temperature and predetermined correction equation stored in the auxiliary memory 6. That is, the bioelectric impedance value is corrected so that change in the bioelectric impedance value based on the change in the body temperature is cancelled. Hereinafter, the bioelectric impedance value corrected in this way is referred to as "the body temperature corrected bioelectric impedance value". Next, the apparatus 1 determines, by a known method, the total amount of body water based on "the body temperature corrected bioelectric impedance value" and the personal particulars inputted at step 5. Hereinafter, the total amount of body water determined based on "the body temperature corrected bioelectric impedance value" is referred to as "the body temperature corrected total amount of body water" (step 13).

Next, the apparatus 1 compares "the body temperature corrected total amount of body water" and the reference body water stored in the auxiliary memory 6, and judges if the dehydration condition is occurring at the time of measuring in step 13. This determination is, for example, based on the ratio of the corrected total amount of body water to the reference body water. When this ratio is substantially 1, it is judged that a dehydration condition is not occurring (step 14), and it is thus shown that the subject's condition is good on the display 3 (step 15). When the above ratio is small, it is judged that the dehydration condition is occurring (step 14), and thus it is shown that the dehydration condition is occurring on the display 3 (step 16).

Upon completion of the judgement whether the dehydration condition is occurring, the apparatus 1 starts to measure the inform time stored in the RAM in the microcomputer 2 by the timer circuit 22 (step 17), and measures the temperature as explained in the section of step 11 (step 18). The apparatus 1 compares the measured the temperature and the reference temperature stored in the RAM (step 19). If the measured temperature is raised more than a predetermined value above the reference temperature, the apparatus 1 updates the inform time stored in the RAM and sets it to a shorter time (step 20).

The apparatus 1 judges whether the inform time measured by the timer circuit 22 has passed (step 21), and when the inform time has passed, the apparatus 1 activates the alarm 23 for urging the subject to examine whether the dehydration condition is occurring (step 22). After that, the apparatus 1 is changed to the measuring mode again, and repeats the measuring of the bioelectric impedance value and the body temperature. In this way, the subject is repeatedly urged to pay attention to examining whether the dehydration condition is occurring, and thus the subject examines whether the dehydration condition occurs repeatedly at appropriate intervals, thus enabling the subject to accurately judge whether the dehydration condition is occurring at an early stage (step 13).

On the other hand, if the inform time has not passed at step 21, the apparatus judges whether the power switch 4A is depressed (step 23). If the power switch 4A is depressed, the apparatus 1 turns off the power and stops operating. If the power switch is not depressed, the apparatus 1 continues to measure the temperature (step 18). In this way, steps 18 to 23 are repeated until the inform time has passed, and the inform time is determined and updated after taking into consideration the change in temperature. Thus, the inform time can be set to urge the subject to pay attention to examining whether the dehydration condition is occurring at more appropriate intervals.

Although a preferred embodiment of the dehydration condition judging apparatus of the present invention has been described above, the present invention is not limited to this embodiment. In this embodiment, the total amount of body water is determined based on the bioelectric impedance value, and whether the dehydration condition is occurring is judged based on the total amount of body water. However, other values can be derived from the bioelectric impedance value, such other values including intra-cellular water, extra-cellular water, a ratio of these waters, electrical resistance of intra-cellular water and extra-cellular water, electrical resistance of intra-cellular water, electrical resistance of extra-cellular water, and a ratio of these resistances. These other values can be used to judge the dehydration condition.

On the other hand, the bioelectric impedance value is increased in the dehydration condition. Thus, using this relation between the dehydration condition and the bioelectric impedance value, the present invention can judge the dehydration condition based on the bioelectric impedance value itself. In this case, it is not necessary to calculate the total amount of body water based on the bioelectric impedance value, and thus it is not necessary to input personal particulars such as height, body weight, sex and age. As a result, it is easy to operate the present apparatus. Thus, the present invention can judge whether the dehydration condition is occurring based on the total amount of body water determined from the bioelectric impedance value, and also judge whether the dehydration condition is occurring based on the bioelectric impedance value itself.

The dehydration condition is related to a subject's pulse in that, when the dehydration condition occurs, the viscosity of blood increases, and as a result the pulse increases rapidly. Thus, the present apparatus may be provided with means for measuring the pulse. The present apparatus may judge the dehydration condition based on the pulse as well as the bioelectric impedance value using the relation between the dehydration condition and the pulse.

When the dehydration condition occurs, the body temperature increases. Thus, the apparatus may judge the dehydration condition based on the body temperature as well as the bioelectric impedance value using the relation between the dehydration condition and the body temperature. Further, the apparatus may judge the dehydration condition based on all of the above factors, namely the bioelectric impedance value, the pulse and the body temperature, which results in a more precise measurement.

In the present embodiment, the bioelectric impedance value is measured using an alternating current of a single frequency. However, the bioelectric impedance value may be measured using a plurality of alternating currents of different frequencies. In this case, it is possible to measure a ratio of intracellular water to extra-cellular water. The inputting of personal particulars such as height, body weight, sex and age is not necessary to calculate this ratio. This ratio does not alter when the body temperature changes. Thus, preferably the dehydration condition may be judged based on the ratio of intra-cellular water to extra-cellular water rather than based on the total amount of body water.

When the humidity is high, a quantity of sweat increases, and thus the dehydration condition is more likely to occur. Thus, the humidity is also a factor causing the dehydration condition to occur. The apparatus may be provided with means for measuring humidity as well as temperature, and the apparatus may determine the inform time based on a change in humidity as well as a change in temperature. In such a way, the inform time will be set to urge the subject to pay attention to examining whether the dehydration condition is occurring at more appropriate intervals.

In addition, in the present embodiment, action levels representing different kinds of exercises are inputted. However, the intensity of an exercise differs from person to person even if their exercises are of the same kind. Thus, one can determine the intensity of exercise only roughly based on the kind of exercise. Thus, the apparatus may be configured to input the intensity of exercise instead of the kind of exercise. This may result in the inform time being set at more appropriate intervals.

In the present embodiment, the body temperature is measured, and the dehydration condition is judged based on the bioelectric impedance value in view of the measured body temperature. However, a temperature of a body surface may be measured instead of the body temperature, and the dehydration condition may be judged based on the bioelectric impedance value in view of the measured body surface temperature.

In the present embodiment, the apparatus urges the subject to pay attention to measuring the bioelectric impedance value by an alarm. However, the apparatus may urge the subject to pay attention by a light or a vibration.

Further, the apparatus may transmit the results of measurement acquired by the apparatus and data relating to the judgement to an outside computer via an input output interface, and the data may be processed in the outside computer. Further, the change in the total amount of body water in a day may be shown on the display of the computer.

As can be understood from the above, the subject can examine whether the dehydration condition is occurring without fail at appropriate times because the apparatus activates an alarm to urge the subject to pay attention to measuring the total amount of body water.

The subject can examine dehydration condition without fail at appropriate times because the inform time is determined according to factors, including age, action level and temperature, which may cause the dehydration condition to occur.

Further, the apparatus of the present invention comprising the body temperature sensor corrects the bioelectric impedance value in accordance with the body temperature, judges the dehydration condition based on the corrected bioelectric impedance, and thus judges the dehydration condition based on the bioelectric impedance in view of the body temperature. Therefore, whether the dehydration condition is occurring can be judged more precisely than in the case of prior art.

What is claimed is:

1. A dehydration condition judging apparatus comprising:
   a bioelectric impedance measuring device;
   a dehydration condition judging unit;
   an judgement result displaying unit;
   an inform time determining unit; and
   an informing device; wherein,
   said bioelectric impedance measuring device supplies an alternating current to a body of a subject and measures a bioelectric impedance value,
   said dehydration condition judging unit judges a dehydration condition of the subject based on the measured bioelectric impedance value,
   said judgement result displaying unit displays the judged dehydration condition,
   said inform time determining unit determines an inform time, and
   said informing device informs the subject at the determined inform time that it is time to measure the total amount of body water.

2. A dehydration condition judging apparatus according to claim 1 wherein;
   said bioelectric impedance measuring device supplies an alternating current of single frequency.

3. A dehydration condition judging apparatus according to claim 1 wherein;
   said bioelectric impedance measuring device supplies a plurality of alternating currents of different frequencies to the subject.

4. A dehydration condition judging apparatus according to any one of claims 1 to 3 further comprising:
   a body temperature measuring device; wherein,
   said body temperature measuring device measures a body temperature of the subject; and
   said dehydration condition judging unit takes into consideration the measured body temperature and then judges the dehydration condition of the subject based on the measured bioelectric impedance value.

5. A dehydration condition judging apparatus according to any one of claims 1 to 4 further comprising:
   an age input unit; wherein;
   said age inputting unit has an age of the subject inputted into; and
   said inform time determining unit determines the inform time based on the inputted age.

6. A dehydration condition judging apparatus according to any one of claims 1 to 5 further comprising:

an action level input unit; wherein;

said action level input unit has an action level of the subject inputted into; and said inform time determining unit determines the inform time based on the inputted action level.

7. A dehydration condition judging apparatus according to any one of claims 1 to 6 further comprising:

a temperature measuring device; wherein;

said temperature measuring device measures a temperature; and said inform time determining unit determines the inform time based on the measured temperature.

8. A dehydration condition judging apparatus according to claim 7, wherein;

said temperature measuring device measures temperature again at least once in a period between the time the inform time is determined and the determined inform time; and said inform time determining unit determines another inform time based on the temperature measured again.

9. A dehydration condition judging apparatus according to claim 7 further comprising:

a humidity measuring device; wherein;

said inform time determining unit determines an inform time based on the measured temperature and humidity.

* * * * *